United States Patent [19]

Michels

[11] 4,348,117

[45] Sep. 7, 1982

[54] APPARATUS AND METHOD FOR MEASURING BOILING OR FLASH PRESSURE OF PRESSURIZED FLUID

[75] Inventor: Donald Michels, Whittier, Calif.

[73] Assignee: Republic Geothermal, Santa Fe, Calif.

[21] Appl. No.: 129,574

[22] Filed: Mar. 12, 1980

[51] Int. Cl.³ .................... G01N 25/08; G01N 7/14
[52] U.S. Cl. .................................. 374/24; 73/64.2; 374/27
[58] Field of Search ............... 73/19, 17 A, 36, 64.2

[56] References Cited

U.S. PATENT DOCUMENTS

| | | | |
|---|---|---|---|
| 2,671,340 | 3/1954 | Jacobs et al. | 73/17 A X |
| 2,722,826 | 11/1955 | Milligan | 73/64.2 |
| 2,782,628 | 2/1957 | Jacobs et al. | 73/64.2 |
| 2,847,852 | 8/1958 | Rhodes et al. | 73/64.2 |

*Primary Examiner*—Charles A. Ruehl
*Attorney, Agent, or Firm*—Curtis, Morris & Safford

[57] ABSTRACT

The pressure of a heated fluid is reduced in a test chamber. A small vent in the upper portion of the test chamber receives a stream of liquid from the chamber and yields a steady hiss when the fluid in the test chamber is under sufficient pressure to maintain the fluid solely in the liquid phase and it yields a sputtering hiss sound when the pressure in the test chamber is reduced sufficiently to permit steam and/or gases to coexist with the liquid in the chamber thus permitting liquid plus vapor to enter the vent. The change in sound may be used to alert an operator and/or pressure fluctuations in the test chamber may be automatically monitored to produce an output signal or a feedback signal for automatic control.

15 Claims, 1 Drawing Figure

APPARATUS AND METHOD FOR MEASURING BOILING OR FLASH PRESSURE OF PRESSURIZED FLUID

BACKGROUND OF THE INVENTION

The present invention relates to sensing the pressure and temperature at which a heated fluid changes from a single phase (liquid) to a 2-phase (liquid-plus-vapor) condition.

Although the invention has general application to detection of the temperature and pressure at which boiling or flashing occurs in a heated fluid, for concreteness of description, an illustrative example is described in which the flash pressure, or pressure and temperature at which steam and/or gases are evolved, is detected in a geothermal liquid.

Geothermal liquids under high pressure in their native rocks generally contain dissolved substances that become gaseous at low pressure, such as $CO_2$, $N_2$, $CH_4$, and many others. The relative proportions and the total amounts of the dissolved gases present depend on the history of the geothermal water.

Exploiting the geothermal water generally involves reducing the total pressures so that dissolved gases escape. If the waer is superheated prior to pressure reduction, some of the water will "flash" to steam and the gases referred to above will mainly follow the steam phase. Since there are several important chemical effects associated with the gas components, it is important to know their concentrations in the geothermal liquid.

One useful indicator of gas concentration is the collective pressure of all the gases as they occur in the unflashed liquid. The collective pressure is the sum of the partial pressures due to individual gas components. The concentration of a single species of gas in the liquid is proportional to its partial pressure in the mixture, but different gases have different proportionality constants. Since the partial pressure of one gas acts independently of the partial pressures of the other gases, the several partial pressures are additive in the mixture. Furthermore, they provide an increment of pressure that exists over and above the vapor pressure of the water of the geothermal fluid. Because of this, a geothermal fluid tends to boil (flash) at a higher pressure than one expects either for pure water at the same temperature or for water dosed with dissolved solids. The latter is the case for geothermal fluids.

This effect has been the basis for an apparatus described by G. D. McDowell in *Geothermics*, v. 3, p. 100, 1974 and by A. J. Ellis and W. A. J. Mahon in *Chemistry and Geothermal Systems*, Academic Press. The described apparatus measures the non-water gas pressures of a geothermal fluid by placing a small chamber of pure $H_2O$ inside a larger chamber in which a mixture of geothermal liquid and vapor achieves thermal equilibrium with the $H_2O$ in the smaller chamber. A differential manometer is used to measure the pressure difference between the chambers. Mathematical equations and certain assumptions convert the measured pressure difference into a concentration of gases.

The method is useful for geothermal fluids which contain more than 1 wt % of gas. The analytical sensitivity is relatively low because the method requires that the boiling (flashing of the geothermal fluid) be fairly advanced in the larger chamber mentioned above. When more water flashes, the other gases are diluted and their pressures are smaller and therefore harder to measure accurately.

U.S. Pat. No. 3,264,863 teaches the use of acoustic input to a fluid to detect cavitation noise indicative of incipient boiling. This apparatus electronically measures the acoustic energy which must be injected into the fluid to produce cavitation noise as the fluid temperature and pressure approach the point at which steam can evolve. The requirement for acoustic input as well as electronic measurement of cavitation noise results in a complex and expensive system.

OBJECTS AND SUMMARY OF THE INVENTION

It is an object of the present invention to provide a method and apparatus for measuring the boiling or flash pressure of a pressurized fluid which overcomes the drawbacks of the prior art.

It is a further object of the invention to provide a method and apparatus for measuring the flash pressure of a heated pressurized geothermal fluid.

It is a further object of the invention to provide a flash pressure detection apparatus having a direct acoustic output.

It is a further object of the invention to provide a flash pressure detection apparatus having an output derived from pressure fluctuations in a test chamber.

The pressure on the geothermal fluid is changed while observing the pressure which marks the boundary between one-phase (all liquid) or 2-phase (mixture of liquid and vapors) conditions. Temperature is also monitored and standard tables give the corresponding pressure for gas-free water. The difference between the flash pressure and the pressure of gas-free water at the same temperature is the total pressure of the dissolved gases. This pressure can be combined with other data to yield more detailed results that have important engineering purposes. The present invention aims toward getting an accurate measure of the flash pressure. Since it measures this pressure at the condition where the smallest amount of vapor has formed, the excess pressures due to dissolved gases are at their maximum values, thus giving good analytical sensitivity.

According to one aspect of the invention, there is provided an apparatus for detecting a boundary pressure in a fluid between an all-liquid condition and a liquid-plus-vapor condition comprising a test chamber, means for passing the fluid through the test chamber, means for controlling the pressure in the test chamber and a small-bore vent in an upper portion of the test chamber effective to vent the liquid when the fluid is in the liquid condition, and to vent liquid plus vapor when the fluid is in the liquid-plus-vapor condition.

According to another aspect of the invention, there is provided an apparatus for detecting a boundary pressure in a fluid between an all-liquid condition and a liquid-plus-vapor condition comprising a test chamber, an inlet conduit for feeding the liquid to the test chamber, an outlet conduit for discharging the fluid from the test chamber, a controllable valve in the outlet conduit for controlling pressure in the test chamber, a small-bore tube communicating an upper portion of the test chamber to atmospheric pressure, and a pressure sensor for sensing the pressure in the test chamber.

According to a feature of the invention, there is provided a method of detecting a boundary pressure in a fluid between an all-liquid condition and a liquid-plus-vapor condition, comprising the steps of passing the fluid through a test chamber, varying the pressure of the fluid in the test chamber through the boundary pressure, venting an upper portion of the test chamber to atmosphere whereby only liquid enters the vent when the pressure is above the boundary pressure and liquid plus vapor enters the vent when the pressure is below the boundary pressure, and determining the boundary pressure in response to a change in a characteristic of the venting.

The above, and other objects, features and advantages of the present invention will become apparent from the following description read in conjunction with the accompanying drawings in which like reference numerals designate the same elements.

DETAILED DESCRIPTION OF THE PREFERRED EMBODIMENT

Figure 1:
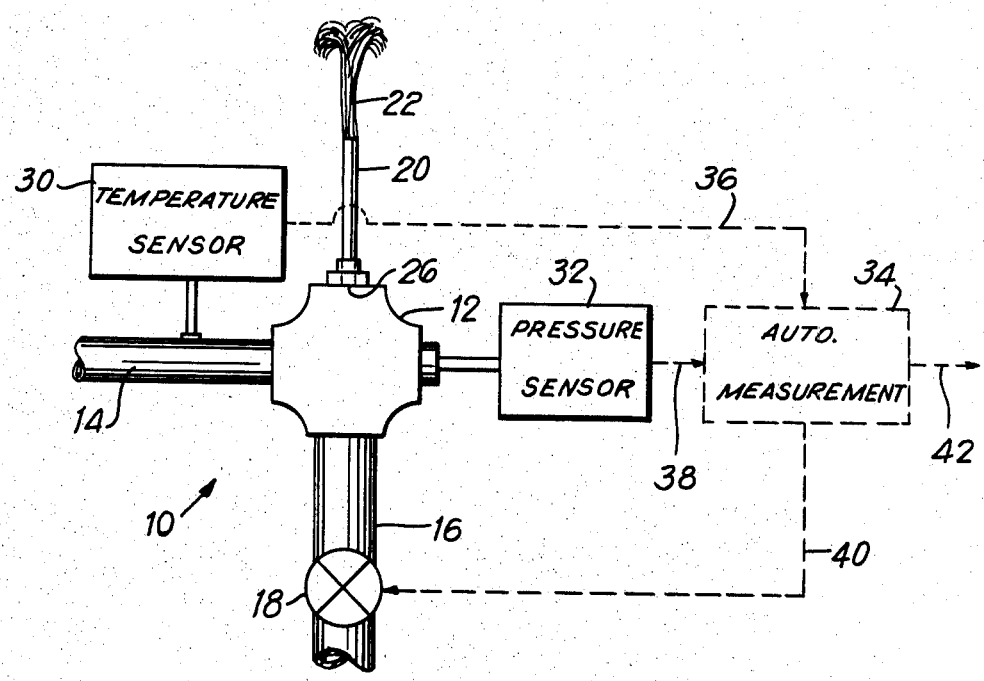
FIG. 1 is a schematic diagram of a flash pressure measurement apparatus according to an embodiment of the present invention.

Referring now to FIG. 1, there is shown generally at 10 a flash-pressure measurement apparatus according to the teaching of the present invention. A test chamber 12 receives a flow of heated pressurized liquid, which may be a geothermal liquid, through an inlet conduit 14 and discharges the fluid through an outlet conduit 16. A controllable valve 18, which may be manually and/or automatically controlled, determines the rate at which fluid may flow through outlet conduit 16 from test chamber 12. A small-bore tube 20 enters an upper portion of test chamber 12 at a point 26 where it vents a stream of liquid and/or vapor 22 from the upper portion of test chamber 12 to a lower pressure region, suitably to atmospheric pressure. Regardless the condition of the fluid as it enters small-bore tube 20, by the time it exits tube 20 to atmospheric pressure, it will normally have flashed to a liquid-plus-vapor condition. When the fluid in test chamber 12 is slightly below the boundary pressure, bubbles appear in the liquid therein. Some of the bubbles occur near enough to the entrance of tube 20 in region 26 that they are accelerated into and swept through tube 20 as part of fluid stream 22. The specific preferred embodiment shows the vent opening at a point 26 in the upper portion of test chamber 12, but is would be clear to one skilled in the art that the invention could also be operated if the vent opening were located elsewhere in the test chamber. The compressibility of the vapor within the bubbles in test chamber 12 may enhance the desired acoustic and pressure oscillation effects.

A temperature sensor 30, which may be a temperature gauge and/or a temperature transducer, senses the temperature of the geothermal fluid in inlet conduit 14. By placing temperature sensor 30 close to test chamber 12, the temperature measured by temperature sensor 30 is a good approximation of the temperature of the geothermal fluid in test chamber 12. A pressure sensor 32, which may be a pressure gauge and/or a pressure transducer, senses the pressure in test chamber 12.

Means is provided for restricting the flow rate through inlet conduit 14 to a value smaller than the flow capacity of outlet conduit 16 when controllable valve 18 is fully opened. Such means may include a constriction (not shown) in inlet conduit 14 or the sizing of inlet conduit 14 substantially smaller than outlet conduit 16 as shown. This permits control of the pressure in test chamber 12 from a value substantially equal to the pressure of the incoming fluid (controllable valve 18 closed) to a value approaching atmospheric pressure (controllable valve 18 fully opened.

The elements thus far described are sufficient for a manually operated system. Before beginning a measurement, fluid is passed through test chamber 12 for long enough for test chamber 12 to be heated to about the temperature of the fluid. Valve 18 may be gradually opened, while the operator listens for the point at which stream 22 into small-bore tube 20 changes from all liquid to a mixture of liquid and vapor indicated by the steady hiss when only liquid enters small-bore tube 20, changing to a sputtering sound when liquid plus vapor enter small-bore tube 20. Alternatively, the operator may observe pressure sensor 32 to detect fluctuations, or water hammer, in pressure within test chamber 12 at the onset of flashing. Prior to flashing, the pressure in test chamber 12 is as steady as, or steadier than, the source pressure. The steady pressure indicated by pressure sensor 32 just before pressure fluctuations are detected, is the flashing pressure. The flashing pressure, combined with the temperature measured by temperature sensor 30, can then be used to determine the total pressure of gases in the geothermal fluid as previously described. Detection may be performed either in the increasing pressure direction by noting the pressure at which sputtering and pressure fluctuations just cease or in the decreasing pressure direction by noting the pressure just before they begin.

An automatic measurement 34 is optionally provided by receiving inputs from temperature sensor 30 on an input line 36 and from pressure sensor 32 on input line 38. Automatic measurement 34 may feed back a control input on control line 40 to controllable valve 18. The control input to controllable valve 18 may continuously ajust controllable valve 18 to maintain the pressure in test chamber 12 in the vicinity of the flash pressure. An output line 42 is optionally provided for transmitting sensed temperature and pressure and/or control outputs to external equipment (not shown). Automatic measurement 34 may include computing apparatus to calculate the total gas pressure based on outputs of temperature sensor 30 and pressure sensor 32 given a priori inputs of dissolved mineral content. The resulting calculation may be provided on output line 42.

Having described a specific preferred embodiment of the invention with reference to the accompanying drawing, it is to be understood that the invention is not limited to this precise embodiment, and that various changes and modifications may be effected therein by one skilled in the art without departing from the scope or spirit of the invention as defined in the appended claims.

What is claimed is:

1. Apparatus for detecting a boundary pressure in a fluid between an all-liquid condition and a liquid-plus-vapor condition comprising:
   a test chamber;
   means for passing said fluid through said test chamber;
   means for controlling pressure of said fluid said test chamber; and
   a small-bore vent in an upper portion of said test chamber effective to vent said liquid from said test chamber, and to vent liquid plus vapor when said fluid is in said liquid-plus-vapor condition.

2. An apparatus according to claim 1; further comprising means for sensing pressure in said test chamber.

3. An apparatus according to claim 2; wherein said boundary pressure is detected by one of the onset and cessation of pressure fluctuations in said test chamber.

4. An apparatus according to claim 2; wherein existence of said boundary pressure is indicated by a change in a sound of said small-bore vent.

5. An apparatus according to claim 2; further comprising means for measuring a temperature of said fluid in said test chamber.

6. An apparatus according to claim 2; wherein said means for controlling said pressure includes automatic control means responsive at least to said means for sensing pressure.

7. An apparatus according to claim 1; wherein said means for passing includes an inlet conduit and an outlet conduit and said means for controlling said pressure includes a controllable valve in said outlet conduit.

8. An apparatus according to claim 7 wherein said means for controlling said pressure further includes said outlet conduit having a greater flow capacity than said inlet conduit.

9. An apparatus according to claim 1; wherein said means for controlling said pressure includes at least a manually controllable valve.

10. An apparatus according to claim 1; wherein said small-bore vent is a small-bore tube.

11. Apparatus for detecting a boundary pressure in a fluid between an all-liquid condition and a liquid-plus-vapor condition comprising:
a test chamber;
an inlet conduit for feeding said liquid to said test chamber;
an outlet conduit for discharging said fluid from said test chamber;
a controllable valve in said outlet conduit for controlling pressure in said test chamber;
a small-bore tube communicating an upper portion of said test chamber to atmospheric pressure; and
a pressure sensor for sensing said pressure in said test chamber.

12. A method of detecting a boundary pressure in a fluid between an all-liquid condition and a liquid-plus-vapor condition, comprising the steps of:
passing said fluid through a test chamber;
varying the pressure of said fluid in said test chamber through said boundary pressure;
venting an upper portion of said test chamber to atmospheric pressure whereby only liquid is vented when said pressure is above said boundary pressure and liquid plus vapor is vented when said pressure is below said boundary pressure; and
determining said boundary pressure in response to a change in a characteristic of said venting.

13. A method according to claim 12; wherein said characteristic of said venting is a change in a sound of said venting.

14. A method according to claim 12; wherein said characteristic of said venting is a pressure fluctuation in said test chamber when said pressure is lower than said boundary pressure and a substantially steady pressure when said pressure is higher than said boundary pressure.

15. Apparatus for detecting a boundary pressure in a fluid between an all-liquid condition and a liquid-plus-vapor condition comprising:
a test chamber;
means for passing said fluid through said test chamber;
means for controlling pressure of said fluid in said test chamber; and
means in said test chamber effective to vent said liquid from said test chamber, and to vent liquid plus vapor when said fluid is in said liquid-plus-vapor condition.

* * * * *